United States Patent
Thornhill et al.

[11] Patent Number: 6,019,765
[45] Date of Patent: Feb. 1, 2000

[54] MORSELLIZED BONE ALLOGRAFT APPLICATOR DEVICE

[75] Inventors: Thomas Thornhill, Dover; William H. Kennefick, Mansfield; Erik Larson, Norwood; Jorge Ochoa, Norton, all of Mass.

[73] Assignee: Johnson & Johnson Professional, Inc., Raynham, Mass.

[21] Appl. No.: 09/073,773

[22] Filed: May 6, 1998

[51] Int. Cl.[7] .............................. A61F 5/04; A61B 17/56
[52] U.S. Cl. .................. 606/94; 606/93; 623/22
[58] Field of Search .................. 606/92, 93, 94, 606/91; 604/207, 208, 211, 218, 224, 264; 623/22

[56] References Cited

U.S. PATENT DOCUMENTS

| | | |
|---|---|---|
| 843,587 | 2/1907 | De Pew . |
| 2,431,985 | 12/1947 | Bowman et al. . |
| 4,184,490 | 1/1980 | Jacklich . |
| 4,232,670 | 11/1980 | Richter et al. . |
| 4,338,925 | 7/1982 | Miller . |
| 5,346,495 | 9/1994 | Vargas, III ........................ 606/92 |
| 5,697,932 | 12/1997 | Smith et al. ...................... 606/80 |
| 5,718,707 | 2/1998 | Mikhail ............................ 606/94 |

*Primary Examiner*—Michael Buiz
*Assistant Examiner*—David O. Reip
*Attorney, Agent, or Firm*—Nutter, McClennen & Fish, LLP

[57] ABSTRACT

A bone allograft applicator device and system is effective to apply a bone graft slurry to an artificial joint without having to remove a previously implanted prosthetic component. In one embodiment, the device includes a hollow member coupled to an actuation mechanism for discharging the bone slurry from the device via a nozzle coupled to a distal end of the hollow member. The device can be used to discharge bone graft slurry from the nozzle and through a screw hole in an acetabular component implanted in the acetabulum of a patient. A bone allograft system can include various components for loading the device with the slurry and/or a plurality of nozzles each having a geometry suited for a particular application.

14 Claims, 4 Drawing Sheets

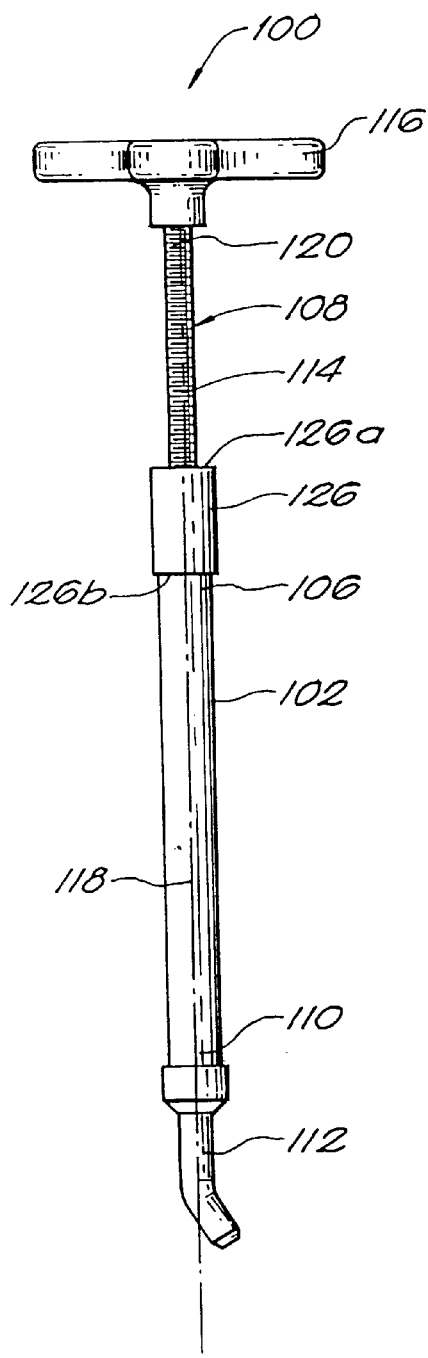
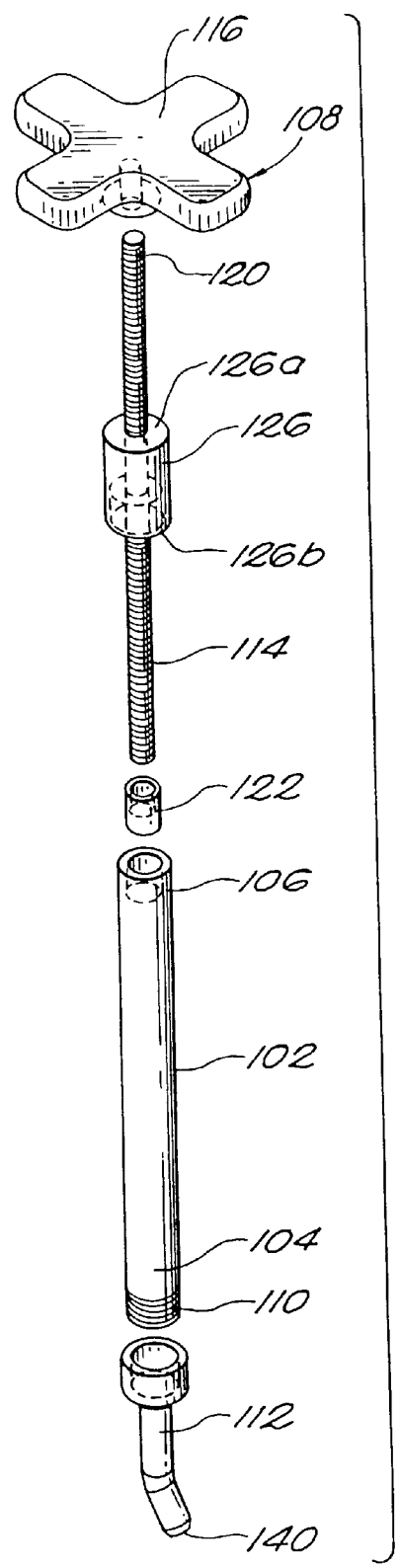
FIG. 1
FIG. 2

6,019,765

MORSELLIZED BONE ALLOGRAFT APPLICATOR DEVICE

CROSS-REFERENCE TO RELATED APPLICATIONS

Not applicable.

STATEMENT REGARDING FEDERALLY SPONSORED RESEARCH

Not applicable.

FIELD OF THE INVENTION

The invention relates to surgical fluid applicator devices, and more particularly to surgical bone graft applicator devices.

BACKGROUND OF THE INVENTION

Many surgical procedures require the use of a bone graft to augment natural bone during a surgical procedure. In orthopedic surgical procedures, particularly joint replacement surgery, certain implantable components must be affixed to bone. The bone quality of a patient, in an area at which a component must be implanted, must be sufficient to enable the effective anchoring of the implant to the bone. During some procedures the bone graft can be properly placed before the implantable component is installed. In some cases, however, it is not until after the implant has been installed that it becomes apparent that there is a need to augment existing bone with a bone graft.

Hip replacement revision surgery is an example of a procedure where bone may need to be augmented after an implantable component is installed. In a total hip replacement surgery, an acetabular cup is implanted in the acetabulum and a femoral component is implanted in the femur of a patient. While some bone ingrowth may occur about an outer portion of the acetabular cup, voids can form between the implanted acetabular shell and the patient's natural acetabulum. This can result in insufficient fixation of the acetabular shell component in the acetabulum. Correction typically requires that the shell be removed and reinstalled after proper augmenting of the bone or re-reaming of the acetabular cavity. Such correction therefore incurs the cost associated with use of an operating room, the cost of the implant and the risk to the patient.

It would be desirable to provide a system and technique to deliver a bone graft to enhance fixation of a prosthetic joint component without having to remove the previously implanted prosthesis.

SUMMARY OF THE INVENTION

The present invention provides a device and system for applying a fluid to a selected location in the body of a patient. Although the invention is primarily shown and described with reference to the application of a bone allograft, it is understood that the device can apply any biocompatible fluid during a surgical procedure.

The present invention comprises a surgical applicator device having a hollow tube with proximal and distal ends. The hollow tube can be filled with a bone graft material of a type well known in the art, which is typically in the form of a slurry. The applicator device further includes at least one delivery nozzle that is removably and replaceably attachable to the distal end of the hollow tube. A plunger rod is removably and replaceably matable within the hollow tube such that it is effective to reciprocate within the hollow tube to selectively eject through the nozzle a fluid, such as a bone graft slurry, which is housed in the hollow tube. In one embodiment, the proximal end of the plunger rod is threadably engaged with the hollow tube so that the distal end of the plunger is effective to push the slurry through the nozzle when the plunger is advanced. To axially displace the plunger, the proximal end of the plunger rod may include an actuating device, such as a crank handle, which enables the plunger rod to be advanced distally in order to eject the slurry from the nozzle.

The nozzle has a main axis and proximal and distal ends with an ejection opening at the distal end thereof. In one embodiment, the ejection opening is co-axial with the main axis of the nozzle. Alternatively, the ejection opening may be oriented with respect to the longitudinal axis of the nozzle. The angular orientation may vary, but preferably it is an acute angle, such as in the range of about 20 to 60°.

The applicator device of the invention may be part of a system that includes the applicator with its hollow tube and plunger rod. The system may also include a selection of nozzles as well as components to facilitate loading of a bone graft slurry within the hollow tube. In one embodiment, the loading components include a funnel component that is selectively matable to the proximal end of the hollow tube to facilitate loading of the slurry into the hollow tube. A packing rod may be used with the funnel tube to properly pack the slurry within the hollow tube. Once the slurry is properly loaded, the funnel and the packing rod are removed. With the hollow tube properly loaded and a nozzle attached, the plunger rod is assembled to the hollow tube and the device is ready for use in a surgical procedure.

BRIEF DESCRIPTION OF THE DRAWINGS

The invention will be more fully understood from the following detailed description taken in conjunction with the accompanying drawings, in which:

FIG. 1 is a side view of a surgical applicator device in accordance with the present invention;

FIG. 2 is an exploded view of the device of FIG. 1;

DETAILED DESCRIPTION OF THE INVENTION

FIG. 1 shows an exemplary embodiment of a bone allograft applicator device 100 in accordance with the present invention. The device 100 is useful for applying a bone graft slurry to a selected location in a prosthetic joint so as to enhance the fixation properties of an implanted prosthetic component without removing and reinstalling the prosthetic component.

Figure 3:
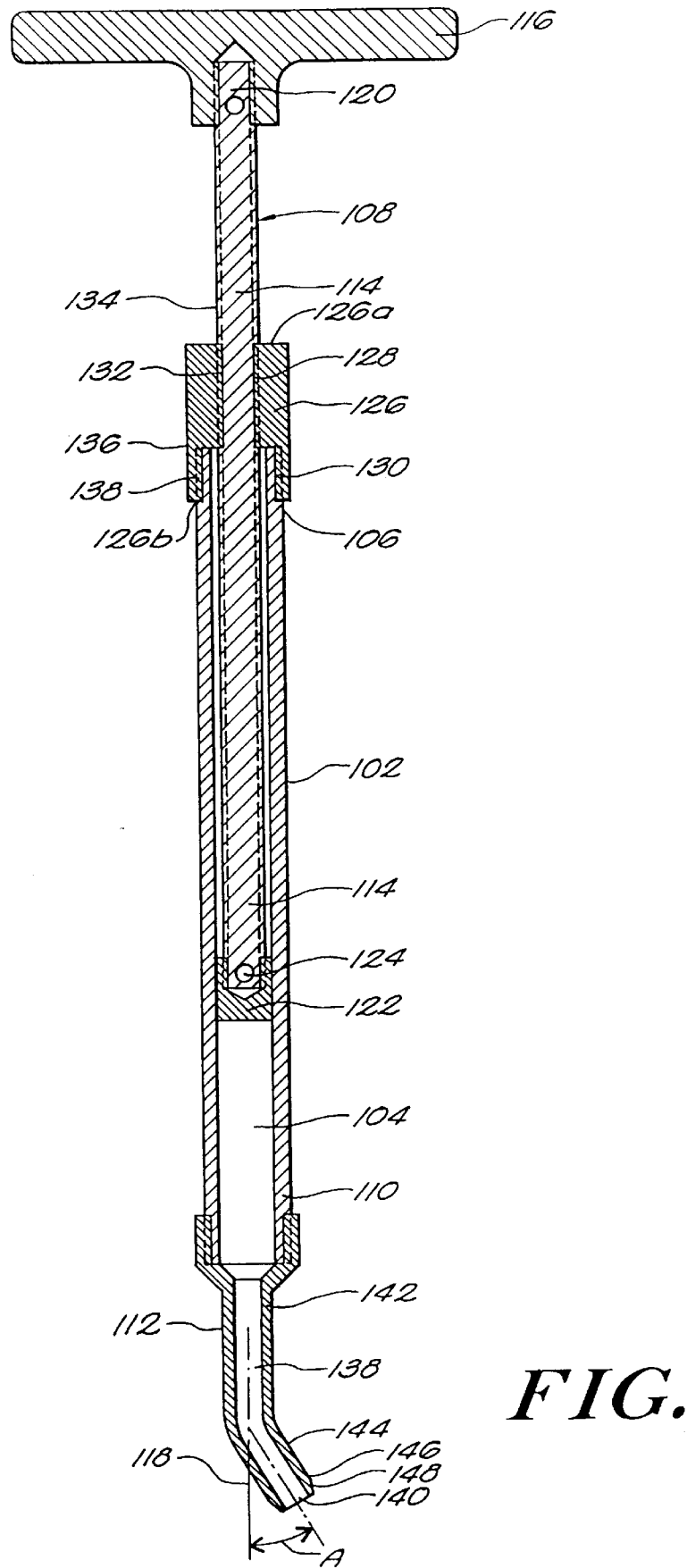
FIG. 3 is a cross-sectional view of the device of FIG. 1.

Referring to FIGS. 2–3 in conjunction with FIG. 1, the device 100 includes a hollow tube member 102 defining a cavity 104 for holding a supply of a bone graft slurry of a type well known to one of ordinary skill in the art. The hollow member 102 has a proximal end 106 that is engageable with an actuation mechanism 108 and a distal end 110 that is matable to a nozzle 112. The actuation mechanism 108 is effective to discharge the bone graft slurry from the device 100 via the nozzle 112 at a controlled rate.

The actuation mechanism 108 can include a variety of structures that can selectively apply pressure to the bone graft material so that it is ejected from the nozzle 112 in desired amounts or flow rates. Exemplary mechanisms include, but are not limited to, plunger mechanisms, pressurization, crank mechanisms, pistons, and trigger mechanisms.

In one embodiment, the actuation mechanism 108 includes a plunger rod 114 matable to a rotatable crank handle 116 for displacing the plunger rod along a main or longitudinal axis 118 of the hollow member 102. The handle 116 is coupled to a proximal end 120 of the plunger rod and a head 122 is coupled to a distal end 124 of the plunger rod. The head 122 should have a geometry such that it allows the plunger rod 114 to slide within the hollow member 102 while sealing the slurry within the cavity 104.

The plunger rod 114 is aligned with the main axis 118 and secured to the hollow member 102 by means of a coupling member 126. In an exemplary embodiment, the coupling member 126 has a proximal surface 126a in which a first bore 128 is formed and a distal surface 126b in which a second bore 130 formed. In one embodiment, the first bore 128 has a threaded inner surface 132 that is threadably engageable with a complementary threaded outer surface 134 of the plunger rod. Rotation of the plunger rod 114 with respect to the coupling member 126 longitudinally displaces the plunger rod within the hollow member 102.

The second bore 130 in the coupling member has a plurality of threads 136 that are engageable with threads 138 disposed on the proximal end 106 of the hollow member. The complementary threads 136,138 securely engage the coupling member 126 to the hollow member 102.

The nozzle 112 is removably and replaceably attachable to the distal end 110 of the hollow member. In one embodiment, the nozzle 112 is threadably engageable with the distal end 110 of the hollow member. The nozzle 112 includes a passageway 138 extending from the cavity 104 and terminating in an ejection port or opening 140. It is understood that the diameter of the of the passageway 138 is selected to achieve a desired rate of discharge for the bone graft slurry. The nozzle 112 can include a diaphragm or other one way type of valve to prevent dripping or excessive slurry discharge. In general, the nozzle 112, in combination with the actuation mechanism 108, should provide controlled ejection of the bone graft slurry from the device.

The nozzle 112 can have a variety of geometries each of which can be adapted for a particular application. In one embodiment, the nozzle 112 has a first portion 142 that is generally coaxial with the main axis 118 of the hollow member and a second portion 144 that forms an angle A with respect to the first portion. The angle A formed by the first and second portions 142,144 is an acute angle, and more preferably can range from about twenty to about sixty degrees. In one embodiment, the angle A is about thirty degrees.

Figure 4:
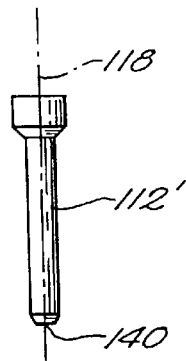
FIG. 4 is a side view of an alternative embodiment of a nozzle forming a portion of a surgical applicator device in accordance with the present invention.

In another embodiment shown in FIG. 4, a nozzle 112' is substantially linear. That is, the ejection opening 140 is coaxial with the main axis 118 of the hollow member 102.

To facilitaten the application of a bone allograft slurry to a prosthetic joint, a distal end 146 of the nozzle 112 has a geometry adapted for engaging a corresponding opening in a prosthetic component. In one embodiment, the distal end 146 of the nozzle is beveled so as to form a mating surface 148 adapted to be countersunk in a top portion of an aperture in a body, such as a screw hole 12 in an acetabular component 10 (FIGS. 9,10), as described below.

Figure 5:
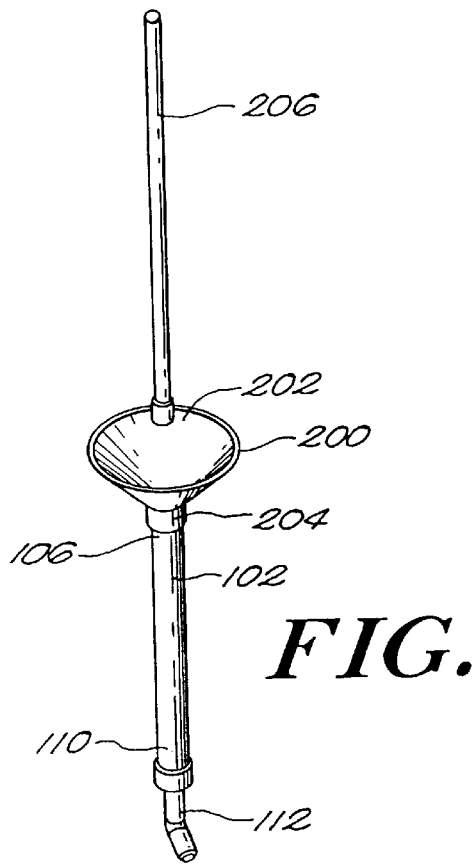
FIG. 5 is a perspective view of a portion of a surgical applicator system in accordance with the present invention showing a surgical applicator device in a configuration adapted for being loaded with a bone graft slurry.

FIGS. 5–8 show an exemplary sequence of steps for assembling a bone allograft system including a bone allograft device in accordance with the present invention, such as the device 100 of FIGS. 1–3. FIG. 5 shows a loading component 200, shown as a funnel, to facilitate placement of a predetermined amount of bone graft slurry within the cavity 104 in the hollow member. In one embodiment, the funnel 200 has an enlarged end 202 for receiving the slurry and a tapered end 204 that is engagable, such as by complementary threads, with the proximal end 106 of the hollow member. Prior to filling the hollow member with the bone graft material, a nozzle 112 that is appropriate for the intended application is selected from a plurality of nozzles having differing sizes and geometries. The nozzle 112 is engaged to the distal end 110 of the hollow member so that the cavity 104 can be filled with a bone graft slurry. The bone graft slurry is then poured into the hollow member 102 via the funnel 200 and optionally packed within the cavity 104 with the aid of a packing rod or tamp 206. After a desired amount of slurry is placed within the device, the funnel 200 is removed from the hollow member 102.

Figure 6:
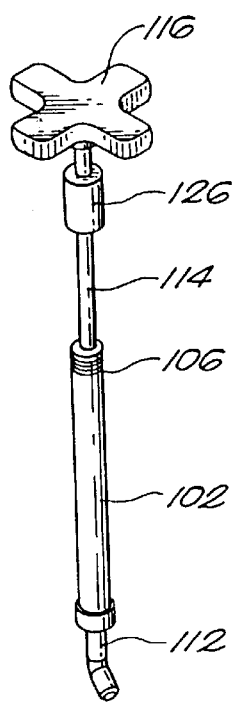
FIG. 6 is a perspective view of the surgical applicator system of FIG. 5 showing the surgical applicator device in a first state of assembly.
Figure 7:
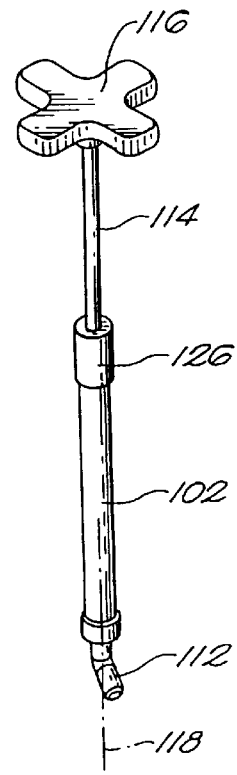
FIG. 7 is a perspective view of the surgical applicator system of FIG. 5 showing the surgical applicator device after assembly.
Figure 8:
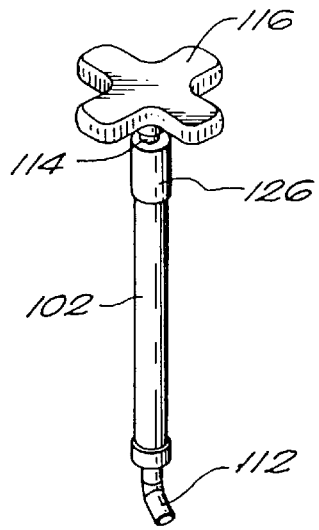
FIG. 8 is a perspective view of the surgical applicator system of FIG. 5 showing the applicator device after the bone graft slurry has been discharged.

As shown in FIG. 6, the plunger rod 114 and head 122 (FIG. 3) are placed within the hollow member 102 until the head rests on the compacted slurry. And as shown in FIG. 7, the coupling member 126 is then threadably engaged with the proximal end 106 of the hollow member so as to seal the bone graft slurry in the cavity 104 (FIG. 3) and align the plunger rod 114 with the main axis 118 of the hollow member. The device is then ready to discharge the bone graft slurry as desired by rotating the crank handle 116 until the chamber 104 is empty, as shown in FIG. 8, where the crank abuts the hollow member 102.

Figure 9:
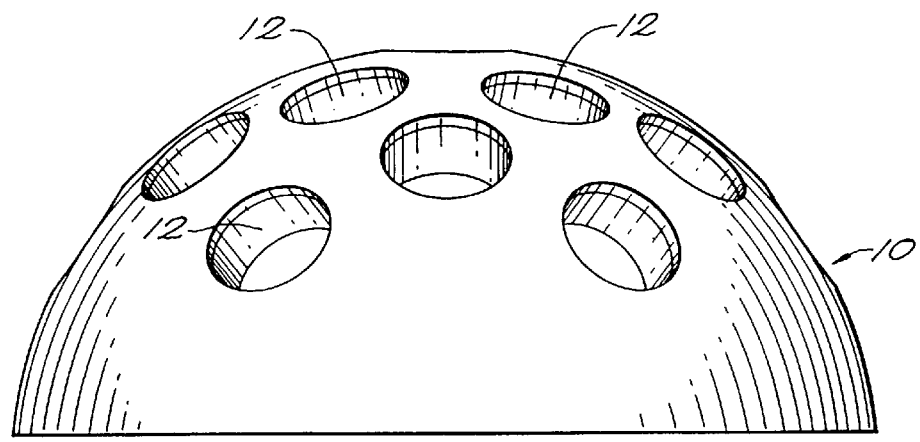
FIG. 9 is a side view of a prior art acetabular component.

The bone allograft applicator device of the present invention is useful to apply a bone graft slurry to a desired location to promote bone ingrowth. In one application, the device is adapted to place bone graft material at a location proximate the prosthesis/bone interface of a previously implanted acetabular cup. An exemplary prior art acetabular cup 10 having a plurality of screw holes 12 is shown in FIG. 9. While the acetabular cup 10 may achieve some degree of fixation due to bone ingrowth about the periphery of the cup, there may be voids at various locations about the dome of the acetabular component. This can result in less than optimal fixation properties for the acetabular cup 10 in the acetabulum. The device of the present invention can fill the voids with bone graft material through openings in the acetabular cup so as to promote bone ingrowth and thereby improve the fixation properties of the implanted acetabular component without surgical removal and re-implantation, such as by revision surgery.

Figure 10:
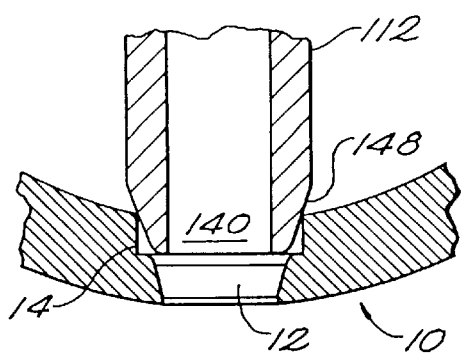
FIG. 10 is a cross-sectional view of a portion of a surgical applicator device in accordance with the present invention shown engaged to the acetabular cup of FIG. 9.

FIG. 10 shows an exemplary embodiment of a device where the nozzle 112 is adapted for alignment with a screw hole 12 in the acetabular component 10 and discharging the bone graft slurry therethrough. More particularly, the mating surface 148 of the nozzle is positioned within an upper portion 14 of the screw hole 12 so as contact the acetabular component 10. It is understood that screw holes in an acetabular component typically have an enlarged opening so as to allow a screw head to be countersunk below a surface of the cup. In general, it is not necessary for the nozzle 112 to form a seal with the acetabular component. The ejection port 140 of the nozzle should be aligned with the screw hole 12 such that bone graft material discharged from the device advances through the acetabular component to fill a void at the bone/prosthesis interface.

One skilled in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety.

What is claimed is:

1. A surgical applicator system, comprising:
    an applicator device including
        a hollow tube having proximal and distal ends;
        at least one nozzle having a proximal end and a distal end, the proximal end being removably and replaceably attachable to the distal end of the hollow tube and the distal end of the nozzle having a geometry that is effective to apply a fluid contained in the hollow tube during a surgical procedure;
        a plunger rod removably and replaceably matable within the hollow tube and effective to reciprocate selectively within the hollow tube to eject the fluid contained in the hollow tube through the at least one nozzle; and
    an acetabular cup having at least one opening formed therein, the geometry of the nozzle distal end being effective to engage the at least one opening for applying the fluid therethrough to fill a void at an interface of the acetabular cup and bone after implantation of the cup.

2. The system of claim 1, wherein the distal end of the nozzle has a beveled surface that is engageable with the opening.

3. The system of claim 1, wherein a fluid ejecting opening of the nozzle is coaxial with a main axis of the nozzle.

4. The system of claim 1, wherein the fluid ejecting opening of the nozzle is oriented at an acute angle with respect to a main axis of the nozzle.

5. The system of claim 1, wherein the proximal end of the nozzle has an internally threaded hub that is threadingly engageable with complementary threads on the distal end of the hollow tube.

6. The system of claim 1, wherein the plunger rod has a proximal end matable with an actuation mechanism that is effective to selectively advance a distal end of the plunger rod in a distal direction.

7. The system of claim 6, wherein the distal end of the plunger rod includes a head having a diameter that substantially matches an inner diameter of the hollow tube member.

8. The system of claim 1, further including a coupling member matable to the proximal end of the hollow tube member, the coupling member being effective to align the plunger rod such that it is coaxial with a longitudinal axis of the hollow tube member.

9. The system of claim 1, further including a plurality of nozzles each having a particular geometry and size.

10. A system for applying a bone graft material to a prosthetic hip joint through an opening in an implanted acetabular cup, comprising:
    a device including
        a hollow tube having a proximal end and a distal end, the hollow tube defining a cavity that is effective to contain a bone graft slurry;
        a plunger rod disposed and longitudinally displaceable within the hollow tube member, the plunger rod having a proximal end and a distal end;
        an actuation mechanism coupled to a proximal end of the plunger rod that is effective to selectively advance the distal end of the plunger rod in a distal direction so as to eject the bone graft slurry from the hollow tube;
        a nozzle having a proximal end and a distal end, the proximal end being removably and replaceably matable to the distal end of the hollow tube member; and
    an acetabular cup having an opening with a distal end and a proximal end, the distal end of the nozzle having a geometry that is effective to engage the proximal end of the opening in the implanted acetabular cup and apply the bone graft slurry to a location proximate a distal end of the opening for filling a void at a bone/cup interface after implantation of the cup.

11. A bone allograft system for an implanted prosthetic joint, comprising:
    a device including
        a hollow tube member having a proximal end and a distal end, the tube member having a cavity that is effective to contain a bone graft slurry;
        an actuation mechanism coupled to the hollow tube member that is effective to selectively discharge the bone graft slurry from the tube member;
        a plurality of nozzles, each of which has a proximal end that is removably and replaceably matable to the distal end of the tube member and a distal end; and
    a plurality of prosthetic components each having at least one aperture formed therein for engaging a corresponding one of the plurality of nozzle distal ends to fill a void at an interface of bone and a respective one of the plurality of prosthetic components.

12. The system of claim 11, wherein the plurality of prosthetic components includes at least one acetabular component.

13. The system of claim 11, wherein at least one nozzle in the plurality of nozzles has at least a portion that is offset from a longitudinal axis of the hollow tube member.

14. The system of claim 11, further including a loading component attachable to the hollow tube member that is effective to load the bone graft slurry in the hollow tube member.

* * * * *